United States Patent [19]

Hendlin et al.

[11] 3,935,309

[45] Jan. 27, 1976

[54] SYNERGISTIC COMBINATIONS OF PHOSPHONOMYCIN AND BACTERIOSTATIC AGENTS

[75] Inventors: David Hendlin, Springfield, N.J.; Justo Martinez Mata; Sagrario Mochales Del Val, both of Madrid, Spain; Edward O. Stapley, Metuchen, N.J.

[73] Assignee: Merck & Co., Inc., Rahway, N.J.

[22] Filed: Sept. 20, 1974

[21] Appl. No.: 507,846

Related U.S. Application Data

[63] Continuation-in-part of Ser. Nos. 655,757, July 25, 1967, abandoned, and Ser. No. 679,165, Oct. 20, 1967, abandoned, Ser. No. 728,059, May 9, 1968, Pat. No. 3,639,590, and Ser. No. 59,761, July 30, 1970, abandoned, and Ser. No. 255,117, May 19, 1972, abandoned.

[52] U.S. Cl. ............................................. 424/114
[51] Int. Cl.$^2$ ........................................ A61K 35/00
[58] Field of Search ................................. 424/114

*Primary Examiner*—Jerome D. Goldberg
*Attorney, Agent, or Firm*—Hesna J. Pfeiffer; J. Jerome Behan

[57] ABSTRACT

Pathogens are controlled by concomitant contact with a phosphonomycin antibiotic and a bacteriostatic chemotherapeutic compound by separate or simultaneous administration. The combined action is especially advantageous in contacting resistant microorganisms and other microorganisms which are oridinarily not controlled by contact with the individual chemotherapeutic agents.

6 Claims, No Drawings

SYNERGISTIC COMBINATIONS OF PHOSPHONOMYCIN AND BACTERIOSTATIC AGENTS

CROSS-REFERENCE TO RELATED APPLICATIONS

This is a continuation-in-part of our earlier filed applications Ser. No. 655,757 and 679,165 filed July 25, 1967 and Oct. 20, 1967, respectively, which are now abandoned, application Ser. No. 728,059 filed May 9, 1968, now U.S. Pat. No. 3,639,590 and Ser. No. 59,761 filed July 30, 1970, now abandoned; and U.S. Ser. No. 255,117, filed May 19, 1972, now abandoned.

BACKGROUND OF THE INVENTION

Although in the past several decades great strides have been made in the control of pathogenic bacteria by various bacteriostatic chemotherapeutic agents such as the sulfa compounds and various antibiotics, these agents are generally quite specific in their action, being for example active against certain gram-negative or gram-positive bacteria. In addition, the use of these chemotherapeutic agents has resulted in the development of mutant strains of pathogens which are resistant to the known bacteriostats.

Accordingly, the search for new agents active against a broad spectrum of pathogens, and in particular against resistant strains, has continued.

The bacteriostatic chemotherapeutic agents are a well known group of compounds which are active in inhibiting the growth of pathogenic bacteria. Thus, antibiotics such as tetracyclines, chloramphenicol, erythromycin, novobiocin, oleandomycin and lincomycin, and other chemotherapeutic active substances such as nalidixic acid and the sulfa compounds are well known bacteriostats which are active in inhibiting the growth of various pathogenic bacteria. A number of these bacteriostatic agents, for example chloramphenicol, exhibit untoward side effects at the dosage necessary to control infections, and therefore their use has been limited; and it has been found desirable to find ways of reducing the dosages of such antibiotics.

Phosphonomycin, a recently discovered antibiotic, is called (-) (cis-1,2-epoxypropyl)phosphonic acid or (-) (1R, 2S)-1,2-epoxypropylphosphonic acid or the nonproprietary name fosfomycin. This antibiotic, and in particular various derivatives thereof such as salts, labile ester and amide derivatives thereof, are valuable antibiotic substances which are active against various gram-negative and gram-positive pathogens such a Escherichia, Klebsiella, Proteus, Pseudomonas, Salmonella, Staphylococcus and Streptococcus bacteria. Because of their outstanding activity and stability, the salts of phosphonomycin such as those of inorganic as well as organic bases represent preferred forms of the antibiotic. The term "phosphonomycin" as used herein includes not only the free acid but also the various derivatives thereof such as the salts, esters and amides which exhibit antibiotic activity.

SUMMARY OF THE INVENTION

It is an object of this invention to provide a method of potentiating the effectiveness of bacteriostatic chemotherapeutic agents against various pathogenic microorganisms. Another object is to provide a means of extending the effectiveness of various bacteriostatic agents against species of microorganisms which are ordinarily not inhibited by the chemotherapeutic agent alone. Further, it is an oject of this invention to provide a means of potentiating the effectiveness of bacteriostatic chemotherapeutic agents against resistant strains of pathogens. In addition, it is an object of this invention to provide a means of preventing the emergence of resistant strains of pathogenic bacteria contacted with bacteriostatic agents. Also, this invention provides new compositions containing bacteriostatic agents useful in accomplishing the foregoing objects of this invention. Other objects will be apparent from the detailed description of this invention hereinafter provided.

DETAILED DESCRIPTION

It has now been found that the foregoing objects of this invention are achieved by concomitantly contacting pathogenic bacteria wtih phosphonomycin and a bacteriostatic chemotherapeutic agent. Thus, in combination with phosphonomycin it is possible to extend the usefulness of the bacteriostats to a broad spectrum of pathogens including this which have mutated and acquired resistance to such chemotherapeutic agents.

In accordance with one embodiment of this invention, pathogenic bacteria are controlled by concomitantly contacting these pathogens with phosphonomycin and a bacteriostatic chemotherapeutic agent. The action of the phosphonomycin is to potentiate, augment or synergise the activity of the bacteriostatic agent. This potentiation of the bacteriostats is indeed unexpected since the bacteriostatic agents have an entirely different mode of action than phosphonomycin. Thus, while many of the bacteriostats such as chloroamphenicol and the tetracyclines are effective because of their ability to inhibit protein synthesis, phosphonomycin is bactericidal in action and affects the bacterial cell wall as is evident from the detection of spheroplasts when certain bacterial strains are exposed to the antibiotic. That phosphonomycin could act synergistically with bacteriostats is not suggested by their individual modes of action. Thus, phosphonomycin is indeed unique among antibiotics in that it is capable of potentiating the important bacteriostatic chemotherapeutic agents. Even more important is the indication that phosphonomycin does not exhibit any antagonism in various tests with human pathogens.

From many in vitro tests with various pathogens, it has been determined that phosphonomycin acts synergistically with a number of bacteriostats such as chloramphenicol, erythromycin, tetracyclines, novobiocin and sulfisoxazole; this synergism being defined as the ability of phosphonomycin to inhibit the growth of the pathogen in the presence of one quarter or less of the MIC (minimum inhibitory concentration) of each of phosphonomycin and the bacteriostat. In an enormous series of tests with almost 200 pathogenic bacteria involving about 15,000 individual tests, the efficacy of phosphonomycin combined with chloramphenicol and erythromycin was determined. These tests indicated that there was no antagonism between phosphonomycin and each of the antibiotics and that in 88% of the tests it was found that phosphonomycin potentiated the effect of chloramphenicol. In a smaller series of trials it was observed that 83% of the tests showed potentiation with a combination of phosphonomycin and erythromycin. Other experimental results have shown that novobiocin, chlortetracycline and sulfisoxazole are potentiated when combined with phosphonomycin and tested with various strains of pathogenic bacteria.

The practical advantages of the use of phosphonomycin to potentiate bacteriostats are, therefore, readily apparent. Thus, in potentiating chloramphenicol the combination acts synergistically, making it possible to use less chloramphenicol than would otherwise be necessary to control the pathogens and thereby minimizing the untoward effects sometimes observed with higher dosage levels of this antibiotic. Also, in some instances, for example in the case of novobiocin, the phosphonomycin potentiates the bacteriostat and the combination is effective in controlling pathogens which cannot be effectively controlled by either antibiotic separately. Also, the potentiating effect of the combined action of the bacteriostat and phosphonomycin results in a lower incidence of resistant strains being formed. These upexpected advantages of th effect of phosphonomycin make this an important and valuable advance in the art. Thus, pathogenic bacteria can be controlled by treatment with phosphonomycin and a bacteriostat in the ratio of 1 part of phosphonomycin to 10 parts of the bacteriostat up to 10 parts of the phosphonomycin to 1 part of the bacteriostat. The preferred ratio is 1 part of phosphonomycin to 4 parts of bacteriostat up to 8 parts of phosphonomycin to 1 part of the bacteriostat.

This ability of phosphonomycin to potentiate, augment or synergise the effectiveness of bacteriostats provides a means of effectively combating bacterial infections in animals and humans. For this purpose phosphonomycin can be administered enterally in the form of tablets, capsules, syrups or suppositories or parenterally as solutions in suitable liquid mediums such as sterile water or isotonic solutions. These pharmaceutical forms of phosphonomycin can be prepared in accordance with procedures well known in the pharmaceutical art. Thus, for example, in treating human infections caused by pathogenic bacteria with phosphonomycin and chloramphenicol, the phosphonomycin is administered in an amount from about 500–4,000 mg./day and the chloramphenicol in an amount from about 500–2,000 mg./ day.

Pursuant to another embodiment of the present invention, phosphonomycin and one or more of the bacteriostatic agents can be combined in a single unit dosage form. For this purpose the chemotherapeutic agents can be combined in suitable unit dosage forms in conjunction with suitable non-toxic solid or liquid diluents or carriers. These dosage unit forms can be used for enteral administration in the form of tablets, capsules, syrups or suppositories or, alternatively, these chemotherapeutic agents can be combined in suitable liquid mediums for parenteral administration. For topical administration the phosphonomycin and the chemotherapeutic bacteriostat can be prepared in the form of salves, ointments and the like in accordance with procedures well known in the art for formulating such compositions.

The examples which follow are provided as illustrative embodiments of our invention.

EXAMPLE 1

The MIC (minimum inhibitory concentration) of phosphonomycin and each of the other antibiotics by itself was determined before the combination synergy experiment was begun, as follows: 2 ml. of a double strength solution in sterile distilled water of the highest strength to be tested (usually 1000γ) was added to a tube of double strength nutrient broth (NB) and mixed thoroughly. Two-fold serial dilutions were then made by transferring 2 ml. to the next tube (1 × NB) and so on for approximately 12 tubes. The tubes were inoculated with one drop each of a 1:50 dilution of a culture adjusted to a Lumetron 60 reading in NB + 0.2% yeast extract so as to provide a concentration of cells of approximately 25,000/ml. The tubes were then incubated at 37°C. and examined for growth at 24, 48 and 72 hours.

In the combination experiment, the MIC value obtained as described above was used as approximately the midpoint of the range to be tested for each of the two antibiotics of the combination. In a manner similar to the above, two-fold dilutions of the first substance in the combination were made except that 1.8 ml. volumes were used and a 2.2 × strength solution of both the antibiotic and the NB were made. The second antibiotic of the combination was added to duplicate rows of serial dilutions of the first substance as follows: 0.2 ml. in NB of a $$\frac{10 \text{ MIC}}{4}$$

and a $$\frac{10 \text{ MIC}}{8},$$

respectively, of the second substance was added to each tube in a row of serial dilutions of the first antibiotic. The final concentration that resulted enabled the determination of the effect of both MIC/4 and MIC/8 of each substance in the presence of from approximately 32 MIC to $$\frac{\text{MIC}}{32}$$

of the other. Inocula were added as in the initial single MIC experiment. The results of these tests are shown in the following table:

| Second Substance | Test Organism | Phosphonomycin MIC | Phosphonomycin MIC in Presence of $\leq \frac{\text{MIC}}{4}$ of 2nd Substance | MIC of 2nd Subst. | MIC of 2nd Subst. In Presence of $\leq \frac{\text{MIC}}{4}$ of PHosphonomycin |
|---|---|---|---|---|---|
| Novobiocin | Proteus vulgaris | 220 | 6.8 | 32 | 3.9 |
| Novobiocin | Pseudomonas stutzeri | >220 | 16 | 32 | 8 |
| Novobiocin | Klebsiella pneumoniae | 750 | 5.8 | 32 | <2 |
| Novobiocin | Staphylococcus | | | | |

| Second Substance | Test Organism | Phosphonomycin MIC | Phosphonomycin MIC in Presence of $\frac{MIC}{4}$ of 2nd Substance | MIC of 2nd Subst. | MIC of 2nd Subst. In Presence of $\frac{MIC}{4}$ of PHosphonomycin |
| --- | --- | --- | --- | --- | --- |
| Novobiocin | aureus | 24 | 48 | 0.06+ | 0.015* |
| Novobiocin | Streptococcus faecalis | 93.6 | 24* | 4 | 4 |
| Erythromycin | Pseudomonas aeruginosa | 186 | 93.6 | 250 | 62.5 |
| Erythromycin | Proteus vulgaris | 48 | 96 | 1000 | 500* |
| Erythromycin | Pseudomonas aeruginosa | 376 | 12 | >16000 | 2000+ |
| Erythromycin | Staphylococcus aureus | >192 | 24 | 8 | 2 |
| Chlortetracycline | Streptococcus faecalis | 96 | 192 | 32 | 16 |
| Chlortetracycline | Proteus vulgaris | 48 | 24* | 2 | 0.25 |
| | Streptococcus faecalis | 48 | 48 | 0.5 | 0.5 |

*Value obtained in the presence of $\frac{MIC}{2}$ instead of $\leq \frac{MIC}{4}$ +Resistant growth present The foregoing table is significant in showing that the potentiating effect of phosphonomycin is observed in eight of the twelve tests, and that in no case was there any evidence of antagonism by the combination of antibiotics. Also significant is the mutual potentiation of the phosphonomycin-novobiocin combination against Klebsiella.

EXAMPLE 2

The "criss-cross" method was used to determine potentiation of chloramphenicol by phosphonomycin. This method involved the simultaneous determination of the MIC (minimum inhibitory concentration) of each member of a pair of antibiotics and of combinations of the two in nutrient broth (NB) containing 0.2% yeast extract (YE). Serial two-fold dilutions were made throughout the experiment, and the starting inoculum consisted of approximately 25,000 cells/ml. of *Staphylococcus aureus*. Incubation was at 37°C. for 24 hours. Identical experiments were performed on two different days.

| Second Subst. | Phosphonomycin | Results: MIC's µg/ml. MIC Phosphonomycin In Presence of $\frac{MIC}{4}$ of 2nd Subst. | CLM* MIC | CLM* MIC In Presence of $\leq \frac{MIC}{4}$ of Phosphonomycin |
| --- | --- | --- | --- | --- |
| CLM* | 62.5 | 15.6 | 7.8 | 2.0 |
| CLM* | 31.2 | ~ 7.8 | 3.9 | 0.5 |

*Chloramphenicol

These results clearly demonstrate the synergistic effect of combinations of phosphonomycin and chloramphenicol against this strain of *Staphylococcus aureus*.

EXAMPLE 3

A series of agar plates were prepared containing varying amounts of phosphonomycin and chloramphenicol and mixtures of the two antibiotics which were then inoculated with various test organisms to determine the minimum inhibitory concentrations (MIC) of the individual antibiotics and the effectiveness of the combination of the two antibiotics.

In these tests the agar plates were prepared by combining 1 ml. of a sterile aqueous solution of the antibiotic with 9 ml. of sterile Mueller Hinton agar, thoroughly mixing the antibiotic solution with the agar and allowing the resulting mixture to solidify. The amount of chloramphenicol in the plates ranged from 0.2 to 409.6 mcg/ml., and the amount of phosphonomycin ranged from 2 to 256 mcg/ml. The exact amounts of the antibiotic or antibiotics present in each of the plates are shown in each of the boxes of the following diagrams.

| Chloramphenicol meg/ml. | Phosphonomycin mcg/ml 0 | 2 | 4 | 8 | 16 | 32 | 64 | 128 | 256 |
| --- | --- | --- | --- | --- | --- | --- | --- | --- | --- |
| 0 | 0/0 | 2/0 | 4/0 | 8/0 | 16/0 | 32/0 | 64/0 | 128/0 | 256/0 |
| 0.2 | 0/0.2 | 2/0.2 | 4/0.2 | 8/0.2 | 16/0.2 | 32/0.2 | 64/0.2 | 128/0.2 | 256/0.2 |
| 0.4 | 0/0.4 | 2/0.4 | 4/0.4 | 8/0.4 | 16/0.4 | 32/0.4 | 64/0.4 | 128/0.4 | 256/0.4 |
| 0.8 | 0/0.8 | 2/0.8 | 4/0.8 | 8/0.8 | 16/0.8 | 32/0.8 | 64/0.8 | 128/0.8 | |
| 1.6 | 0/1.6 | 2/1.6 | 4/1.6 | 8/1.6 | 16/1.6 | 32/1.6 | 64/1.6 | | |
| 3.2 | 0/3.2 | 2/3.2 | 4/3.2 | 8/3.2 | 16/3.2 | 32/3.2 | | | |
| 6.4 | 0/6.4 | 2/6.4 | 4/6.4 | 8/6.4 | | | | | |
| 12.8 | 0/12.8 | 2/12.8 | 4/12.8 | ↓ | | | | | |
| 25.6 | 0/25.6 | 2/25.6 | 4/25.6 | ↓ | | | | | |

|  | Phosphonomycin mcg/ml. | | | | | | | | |
|---|---|---|---|---|---|---|---|---|---|
| Chloramphenicol mcg/ml. | 0 | 2 | 4 | 8 | 16 | 32 | 64 | 128 | 256 |
| 0 | 0/0 | 2/0 | 4/0 | 8/0 | 16/0 | 32/0 | 64/0 | 128/0 | 256/0 |
| 12.8 | 0/12.8 | 2/12.8 | 4/12.8 | 8/12.8 | 16/12.8 | 32/12.8 | 64/12.8 | 128/12.8 | 256/12.8 |
| 25.6 | 0/25.6 | 2/25.6 | 4/25.6 | 8/25.6 | 16/25.6 | 32/25.6 | 64/25.6 | 128/25.6 | |
| 51.2 | 0/51.2 | 2/51.2 | 4/51.2 | 8/51.2 | 16/51.2 | 32/51.2 | 64/51.2 | | |
| 102.4 | 0/102.4 | 2/102.4 | 4/102.4 | 8/102.4 | | | | | |
| 204.8 | 0/204.8 | 2/204.8 | 4/204.8 | | | | | | |
| 409.6 | 0.409.6 | 2/409.6 | 4/409.6 | | | | | | |

The described tests were run in either of above-described series, depending upon the activity of the pathogen in disc plate tests, with discs containing 5 μg and 30 μg of chloramphenicol. When the pathogens were inhibited at both the 5 and 30 μg levels, the pathogen was tested in the first series containing lower concentrations of chloramphenicol. The organisms which were not inhibited at the lower level but were inhibited at the 30 μg level were tested in the second series having a higher concentration of chloramphenicol.

Thus, in this series of tests the agar plates contained phosphonomycin and/or chloramphenicol in the amount shown in the numerator and the denominator, respectively, in each of the boxes. (To avoid needless repetition of the concentrations of the antibiotics, only a representative number of the boxes show the concentrations of each of the combinations tested; however, all of the concentrations indicated by each of the boxes were used in tests.)

The plates prepared as described above were divided into small sections or boxes so that each section served to test a different species or different organism. Thus, each section of the plate was inoculated with a different strain or species by placing one drop of an aqueous suspension of the microorganism containing about 10,000–20,000 cells. The plates were then incubated for 18 hours at 37°C. and then examined to determine the MIC of the individual antibiotics and the effectiveness of the combinations of the antibiotics against a number of pathogenic organisms.

The results of this series of tests are shown in the following table.

(EM) against ten strains of pathogenic bacteria was determined with the following results:

| No. of Strains Tested | 10 |
|---|---|
| No Effect | 1 |
| Potentiation by PM | 5 |
| Potentiation by EM | 4 |

EXAMPLE 5

To determine the interaction in vivo of phosphonomycin, chloramphenicol, novobiocin and tetracycline, each agent was titrated individually in mice and in the presence of constant quantities (one estimated to be 10% and a second 1% of the expected $ED_{50}$) of the second antibiotic. For example, using *Escherichia coli* 2017 as the infecting agent, sodium phosphonomycin was titrated alone and in the presence 5 and also in the presence of 0.5γ tetracycline, while tetracycline was titrated alone and in the presence of 50γ, and also in the presence of 5γ of sodium phosphonomycin. The two drugs were given by the subcutaneous route at separate sites on the ventral surface of the mouse. Such therapy was given only at the time of infection for the *Escherichia coli* and *Pseudomonas aeruginosa* tests but both at the time of infection and 6 hours later for all other tests. Infection was given intraperitoneally using broth suspensions of the test organism.

In the first test using *Escherichia coli* with sodium phosphonomycin and tetracycline, the $ED_{50}$ for sodium phosphonomycin was 1000γ, an amount representing, therefore, 100% of the effective sodium phosphonomycin dose. The $ED_{50}$ for tetracycline was 50γ, equaling

| Microorganism | No. Strains Tested | High Potentiation Observed | Weak Potentiation Observed | Additive Coaction | No Effect |
|---|---|---|---|---|---|
| *Escherichia coli* | 81 | 38 | 39 | 2 | 2 |
| *Paracoli* | 2 | 1 | 1 | 0 | 0 |
| *Citrobacter* | 6 | 1 | 3 | 0 | 2 |
| *Aerobacter* | 2 | 1 | 1 | 0 | 0 |
| *Klebsiella* | 27 | 16 | 9 | 0 | 2 |
| *Salmonella* | 4 | 0 | 2 | 0 | 2 |
| *Proteus* | 6 | 3 | 2 | 0 | 1 |
| *Pseudomonas* | 11 | 6 | 3 | 0 | 2 |
| *Serratia* | 2 | 2 | 0 | 0 | 0 |
| *Staphylococcus coagulase+* | 5 | 1 | 2 | 0 | 2 |
| *Staphylococcus* | 43 | 17 | 20 | 3 | 3 |
| *Enterococcus* | 4 | 0 | 3 | 0 | 1 |
| Total | 193 | 86 | 85 | 5 | 17 |

EXAMPLE 4

In another series of tests carried out following the procedures described in Example 3, the effect of combinations of phosphonomycin (PM) and erythromycin 100% of the effective tetracycline dose. When sodium phosphonomycin was titrated in the presence of 0.5γ tetracycline (here representing 1% of the effective tetracycline $ED_{50}$), the sodium phosphonomycin $ED_{50}$ was again 1000γ or 100% of its effective dose. The combination, therefore, of 100% with 1% or 101% of the combined effective doses was judged to indicate no interaction for this combination. When, however, tetracycline was titrated in the presence of a constant quantity of 50γ sodium phosphonomycin (representing 5% of its effective dose), the tetracycline ED$_{50}$ was 13γ or 25% of its effective dose. The combined percent of 30 was as effective as 100% of either drug along, an effect usually termed as synergistic.

On Table 1 are listed the test results using *Escherichia coli*. It can be seen that in two tests the activity of tetracycline has been enhanced when it was titrated in the presence of a constant quantity of sodium phosphonomycin. In the first test, a combination of 25% tetracycline with 5% sodium phosphonomycin for 30% is judged synergistic, but the combination of 54% tetracycline with .5% sodium phosphonomycin is judged to be borderline and not labeled as synergy. In the second test there was synergy with a constant quantity of 2% of the effective sodium phosphonomycin dose but not with 14%. In neither test did a constant quantity of tetracycline enhance sodium phosphonomycin activity. Similarly, it can be seen that synergy has been demonstrated between chloramphenicol and sodium phosphonomycin but that the two tests do not completely repeat each other.

On Table 2 are listed results from single tests. It will be noted that against *Streptococcus pyogenes* only one set of combinations was tested, that is, the titration of tetracycline in the presence of a constant quantity of sodium phosphonomycin. Only additive percentages were demonstrated. In experiments using novobiocin, it is difficult to interpret results because novobiocin itself did not protect against *Pseudomonas aeruginosa*, nor against *Klebsiella pneumoniae* at the levels tested. For this latter organism, however, less sodium phosphonomycin was required to protect the mice when 1 mg. of novobiocin was included in the dose than in its absence. This could be considered as potentiation.

Table I

| Test Organism and Challenge Dose | Effect of Combined Antibiotic Therapy of *Escherichia coli* Infection | | | | | |
|---|---|---|---|---|---|---|
| | Phosphonomycin* plus | s.c. ED$_{50}$ μg*** | | % ED$_{50}$ | | Combined % |
| | | Phosphonomycin* | Other | Phosphonomycin* | Other | |
| *E. coli* 2017 9 LD$_{50}$ | Tetracycline | 1000 | — | 100 | | 100 |
| | | — | 50 | | 100 | 100 |
| | | 427** | 5 | 43 | 10 | 53 |
| | | 1000** | 0.5 | 100 | 1 | 101 |
| | | 50 | 13** | 5 | 25 | 30 |
| | | 5 | 27** | ).5 | 54 | 55 |
| Repeat Test *E. coli* 2017 7 LD$_{50}$ | Tetracycline | 350 | — | 100 | | |
| | | — | 31 | | 100 | |
| | | 390** | 10 | 111 | 32 | 143 |
| | | 380** | 1 | 108 | 3 | 111 |
| | | 50 | 31** | 14 | 100 | 114 |
| | | 0.5 | 7** | 2 | 23 | 25 |
| *E coli* 2017 9 LD$_{50}$ | Chloramphenicol | 905 | — | 100 | | |
| | | — | 453 | | 100 | |
| | | 500** | 30 | 55 | 7 | 63 |
| | | 905** | 3 | 100 | 1 | 101 |
| | | 100 | 107** | 11 | 24 | 35 |
| | | 10 | 250** | 1 | 55 | 56 |
| Repeat Test *E. coli* 2017 7 LD$_{50}$ | Chloramphenicol | 276 | — | 100 | | |
| | | — | 120 | | 100 | |
| | | 26** | 50 | 9 | 42 | 51 |
| | | 92** | 5 | 33 | 4 | 37 |
| | | 50 | 20** | 19 | 17 | 36 |
| | | 5 | 47** | 2 | 39 | 41 |

*As sodium salt
**Titrated—other agent constant
***Single dose only, at 0 hour

Table 2

| Test Organism and Challenge Dose | Effect of Combined Antibiotic Therapy on Several Experimental Infections in Mice | | | | | |
|---|---|---|---|---|---|---|
| | Phosphonomycin* plus | s.c. ED$_{50}$ μg*** | | % ED$_{50}$ | | Combined % |
| | | Phosphonomycin* | Other | Phosphonomycin* | Other | |
| *Streptococcus pyogenes* 3009 6 LD$_{50}$ | Tetracycline | 1400 | — | 100 | 100 | |
| | | — | 55 | | 100 | |
| | | 1000 | 18** | 71 | 33 | 104 |
| | | 500 | 35** | 64 | 36 | 100 |
| *Pseudomonas aeruginosa* 3210 10 LD$_{50}$ | Novobiocin | 1420 | — | 100 | | |
| | | — | >10000 | | | |
| | | 2760** | 1000 | 195 | | |
| | | 1250** | 100 | 88 | | |
| | | >200 | >10000* | | | |
| | | >20 | >10000** | | | |
| *Klebsiella pneumoniae* "B" 7 LD$_{50}$ | Novobiocin | 2130 | — | 100 | | |
| | | — | >2500 | | | |
| | | 298** | 1000 | 14 | — | |
| | | 1110** | 100 | 52 | — | |
| | | >100 | >2500** | | | |
| | | >10 | >2500 | | | |

*As sodium salt
**Titrated —other agent constant
*** Therapy given at 0 and at 6 hours except *P. aeruginosa* 3210, 0 hour only Various changes and modifications in the procedures herein disclosed will occur to those skilled in the art, and to the extent that such changes and modifications are embraced by the appended claims, it is to be understood that they constitute part of our invention.

What is claimed is:

1. A composition comprising a phosphonomycin antibiotic, chloramphenicol and a non-toxic carrier, said phosphonomycin and said chloramphenicol being present in the ratio of 1–10 to 10–1.

2. The composition of claim 1 wherein the carrier is a solid pharmaceutical carrier.

3. The composition of claim 1 wherein the carrier is a liquid pharmaceutical carrier.

4. The composition of claim 1 wherein the phosphonomycin antibiotic is a non-toxic pharmaceutically acceptable salt of phosphonomycin.

5. The method of treating infections caused by pathogenic bacteria in animals and humans which comprises administering to animals or humans a composition comprising phosphonomycin and chloramphenicol in an effective amount for treating said pathogen, said phosphonomycin and chloramphenicol being administered in the ratio of 1–10 to 10–1.

6. The method for controlling resistant pathogenic bacteria in animals and humans which comprises administering to animals or humans a composition comprising phosphonomycin and chloramphenicol in an effective amount for treating said resistant pathogen, said phosphonomycin and chloramphenicol being administered in the ratio of 1–10 to 10–1.

* * * * *